United States Patent
Hagn (10) Patent No.: US 11,160,623 B2
(45) Date of Patent: Nov. 2, 2021

(54) ROBOTIC SURGICAL SYSTEMS AND ROBOTIC ARMS THEREOF

(71) Applicant: Covidien LP, Mansfield, MA (US)

(72) Inventor: Ulrich Hagn, Munich (DE)

(73) Assignee: Covidien LP, Mansfield, MA (US)

(*) Notice: Subject to any disclaimer, the term of this patent is extended or adjusted under 35 U.S.C. 154(b) by 187 days.

(21) Appl. No.: 16/079,572

(22) PCT Filed: Feb. 24, 2017

(86) PCT No.: PCT/US2017/019241
§ 371 (c)(1),
(2) Date: Aug. 24, 2018

(87) PCT Pub. No.: WO2017/147353
PCT Pub. Date: Aug. 31, 2017

(65) Prior Publication Data
US 2019/0069964 A1    Mar. 7, 2019

Related U.S. Application Data

(60) Provisional application No. 62/300,357, filed on Feb. 26, 2016.

(51) Int. Cl.
*A61B 34/37* (2016.01)
*F16H 35/18* (2006.01)
(Continued)

(52) U.S. Cl.
CPC .............. *A61B 34/37* (2016.02); *A61B 17/28* (2013.01); *A61B 34/00* (2016.02); *A61B 34/30* (2016.02);
(Continued)

(58) Field of Classification Search
CPC ......... A61B 34/00; A61B 34/30; A61B 34/37; A61B 17/28; F16H 25/02; F16H 25/20; F16H 35/18
See application file for complete search history.

(56) References Cited

U.S. PATENT DOCUMENTS

| 4,270,404 A | 6/1981 | Murakoshi et al. |
| 6,325,808 B1 | 12/2001 | Bernard et al. |

(Continued)

FOREIGN PATENT DOCUMENTS

| JP | 54142483 | 11/1979 |
| JP | S6396350 A | 4/1988 |

(Continued)

OTHER PUBLICATIONS

European Search Report dated Jan. 16, 2020, corresponding to counterpart European Application No. 17757254.2; 21 pages.
(Continued)

*Primary Examiner* — Tuan V Nguyen (57) ABSTRACT

A robotic arm configured to support and operate a surgical instrument includes a slider, first and second nuts rotatably disposed within the slider, a gear, and left-handed and right-handed lead screws. The first and second nuts each have a geared outer surface operably coupled to the gear. The left-handed lead screw extends through the slider and threadingly engages the first nut. The right-handed lead screw is disposed in parallel relation with the left-handed lead screw and extends through the slider. The right-handed lead screw threadingly engages the second nut. A rotation of the left-handed lead screw and/or the right-handed lead screw effects a rotation of the gear relative to the slider or an axial movement of the slider and the gear along the lead screws.

20 Claims, 11 Drawing Sheets (51) Int. Cl.
  *F16H 25/20* (2006.01)
  *A61B 17/28* (2006.01)
  *A61B 34/00* (2016.01)
  *A61B 34/30* (2016.01)

(52) U.S. Cl.
  CPC ............. *F16H 25/20* (2013.01); *F16H 35/18* (2013.01); *F16H 2025/2081* (2013.01)

(56) References Cited

U.S. PATENT DOCUMENTS

| | | |
|---|---|---|
| 2001/0013764 A1 | 8/2001 | Blumenkranz et al. |
| 2004/0049205 A1* | 3/2004 | Lee ..................... A61B 34/30 606/130 |
| 2009/0163931 A1 | 6/2009 | Cooper et al. |
| 2009/0308188 A1* | 12/2009 | Yang ..................... B25J 9/104 74/89.27 |
| 2012/0116416 A1 | 5/2012 | Neff et al. |
| 2013/0274761 A1 | 10/2013 | Devengenzo et al. |
| 2013/0325030 A1 | 12/2013 | Hourtash et al. |

FOREIGN PATENT DOCUMENTS

| | | |
|---|---|---|
| JP | H11507252 A | 6/1999 |
| WO | 9639944 A1 | 12/1996 |
| WO | 2015142933 A1 | 9/2015 |

OTHER PUBLICATIONS

Australian Office Action dated Oct. 26, 2020, issued in corresponding AU Appln. No. 2017223829, 5 pages.
Chinese Office Action dated Sep. 2, 2020, issued in corresponding Chinese Application No. 201780011867, 14 pages.
Indian Office Action dated May 15, 2021, issued in corresponding Indian Application No. 201817030769, 6 pages (including translation).
Japanese Office Action dated Feb. 1, 2021, issued in corresponding JP Appln. No. 2018543372, 6 pages.
International Search Report dated Jun. 5, 2017, issued in corresponding international application No. PCT/US2017/019241, 4 pages.

* cited by examiner

ROBOTIC SURGICAL SYSTEMS AND ROBOTIC ARMS THEREOF

CROSS-REFERENCE TO RELATED APPLICATIONS

This application is a U.S. National Stage Application filed under 35 U.S.C. § 371(a) of International Patent Application Serial No. PCT/US2017/019241, filed Feb. 24, 2017, which claims the benefit of and priority to U.S. Provisional Patent Application Ser. No. 62/300,357, filed Feb. 26, 2016, the entire disclosure of which is incorporated by reference herein.

BACKGROUND

Robotic surgical systems have been used in minimally invasive medical procedures. Some robotic surgical systems included a console, which supported a surgical robotic arm, and a surgical instrument having at least one end effector (e.g., forceps or a grasping tool) mounted to the robotic arm. The robotic arm provided mechanical power to the surgical instrument for its operation and movement. Each robotic arm may have included an instrument drive unit operatively connected to the surgical instrument.

The robotic arm was comprised of a plurality of segments pivotably coupled to one another through joints. The segments of the robotic arm provided four degrees of freedom of movement for the attached surgical instrument. Current robotic arms have most of their mass towards their bases, which increases inertia thereby decreasing performance.

A need exists for a robotic arm having improved and increased usability, increased structural integrity, with easier assembly and serviceability, and a more compact design while maintaining a multiplicity of degrees of freedom.

SUMMARY

In accordance with an aspect of the present disclosure, a robotic arm configured to support and operate a surgical instrument is provided. The robotic arm includes a slider, first and second nuts rotatably disposed within the slider, a gear, and left-handed and right-handed lead screws. The first and second nuts each have a geared outer surface operably coupled to the gear. The left-handed lead screw extends through the slider and threadingly engages the first nut. The right-handed lead screw is disposed in parallel relation with the left-handed lead screw and extends through the slider. The right-handed lead screw threadingly engages the second nut. A rotation of the left-handed lead screw and/or the right-handed lead screw effects a rotation of the gear relative to the slider or an axial movement of the slider and the gear along the lead screws.

In some embodiments, rotation of the lead screws in opposite directions relative to one another may cause the lead screws to rotate relative to the first and second nuts to drive an axial movement of the first and second nuts and the slider along the lead screws. Rotation of the lead screws in the same direction relative to one another may rotate the first and second nuts to drive a rotation of the gear relative to the slider.

It is contemplated that the robotic arm may further include a housing connected to the slider. The gear may be rotatably disposed within the housing and axially constrained within the housing. The housing and the slider may be configured to move axially together along the lead screws. The housing may define a passageway therethrough configured for passage of a surgical instrument.

It is envisioned that the gear may be configured for non-rotatable receipt of a surgical instrument such that rotation of the gear effects rotation of a surgical instrument disposed therein.

In some embodiments, the robotic arm may further include a first motor operably coupled to the left-handed lead screw, and a second motor operably coupled to the right-handed lead screw such that the lead screws are independently rotatable relative to one another.

It is contemplated that the robotic arm may further include an elongate link having the slider slidably disposed therein and the lead screws rotatably disposed therein. The lead screws may be axially fixed within the elongate link.

It is envisioned that the slider may define a first passageway therethrough and a second passageway therethrough. The first nut may be disposed coaxially with the first passageway and the second nut may be disposed coaxially with the second passageway. The slider may define a side opening therein, from which the geared outer surface of each of the first and second nuts outwardly project.

In another aspect of the present disclosure, a robotic surgical system is provided and includes a surgical instrument and a robotic arm. The robotic arm includes a first elongate link, a second elongate link pivotably coupled to the first elongate link, a slider slidably disposed within the second elongate link, first and second nuts rotatably disposed within the slider, a gear, and left-handed and right-handed lead screws. The nuts each have a geared outer surface operably coupled to the gear. The gear is configured to non-rotatably receive the surgical instrument. The left-handed lead screw extends through the slider and threadingly engages the first nut. The right-handed lead screw is disposed in parallel relation with the left-handed lead screw and extends through the slider. The right-handed lead screw threadingly engages the second nut. A rotation of the left-handed lead screw and/or the right-handed lead screw effects a rotation of the gear relative to the slider or an axial movement of the slider and the gear along the lead screws.

In some embodiments, rotation of the gear may effect rotation of the surgical instrument when the surgical instrument is disposed in the gear.

It is contemplated that the lead screws may be axially fixed within the second elongate link and the slider may be axially movable within the second elongate link.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein:

FIGS. 8A-12A are front views of the multi-directional movement mechanism of FIG. 3 illustrating the various directions of movement of a slider of the multi-directional movement mechanism; and FIGS. 8B-12B are top views of the multi-directional movement mechanism of FIG. 3 illustrating the various directions of movement of a gear/cogwheel of the multi-directional movement mechanism.

DETAILED DESCRIPTION

Embodiments of the presently disclosed robotic surgical system including a robotic arm, a multi-directional movement mechanism of the robotic arm, and a surgical instrument, and methods of making and using the aforementioned, are described in detail with reference to the drawings, in which like reference numerals designate identical or corresponding elements in each of the several views. As used herein the term "distal" refers to that portion of the robotic arm and/or surgical instrument that is closer to the patient, while the term "proximal" refers to that portion of the robotic arm and/or surgical instrument that is farther from the patient. As used herein, the terms clockwise and counterclockwise are rotational directions about an axis when looking in a distal direction along the axis.

Figure 1:
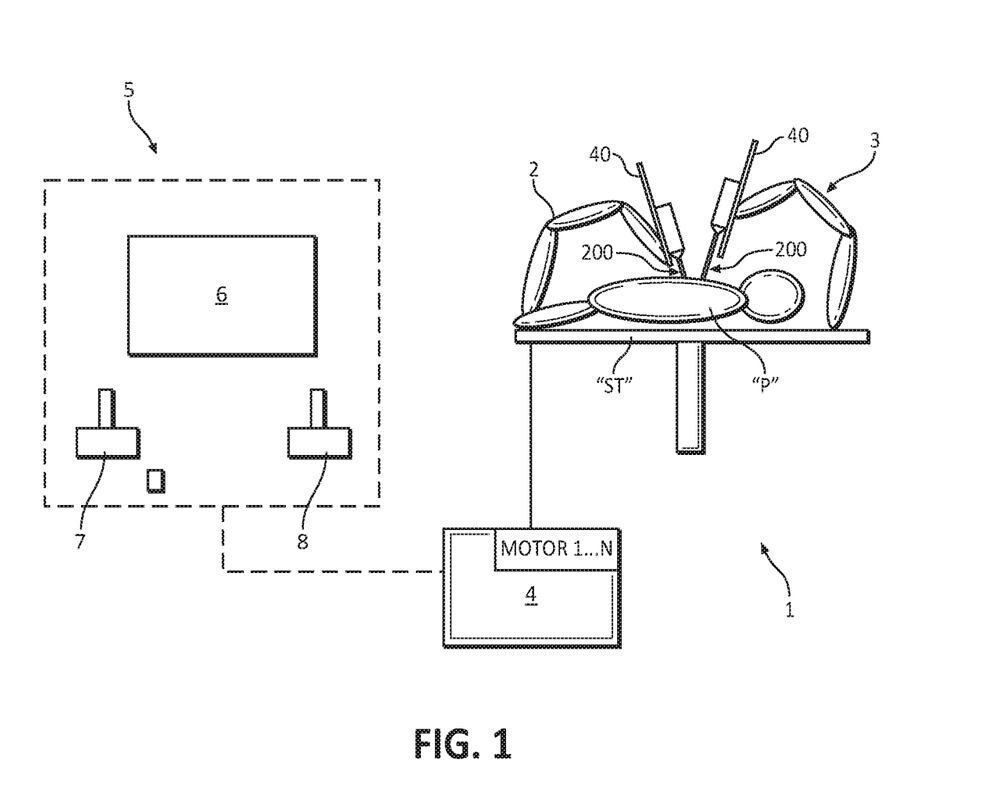
FIG. 1 is a schematic illustration of a robotic surgical system including a surgical robotic arm and a surgical instrument attached thereto.
Figure 2:
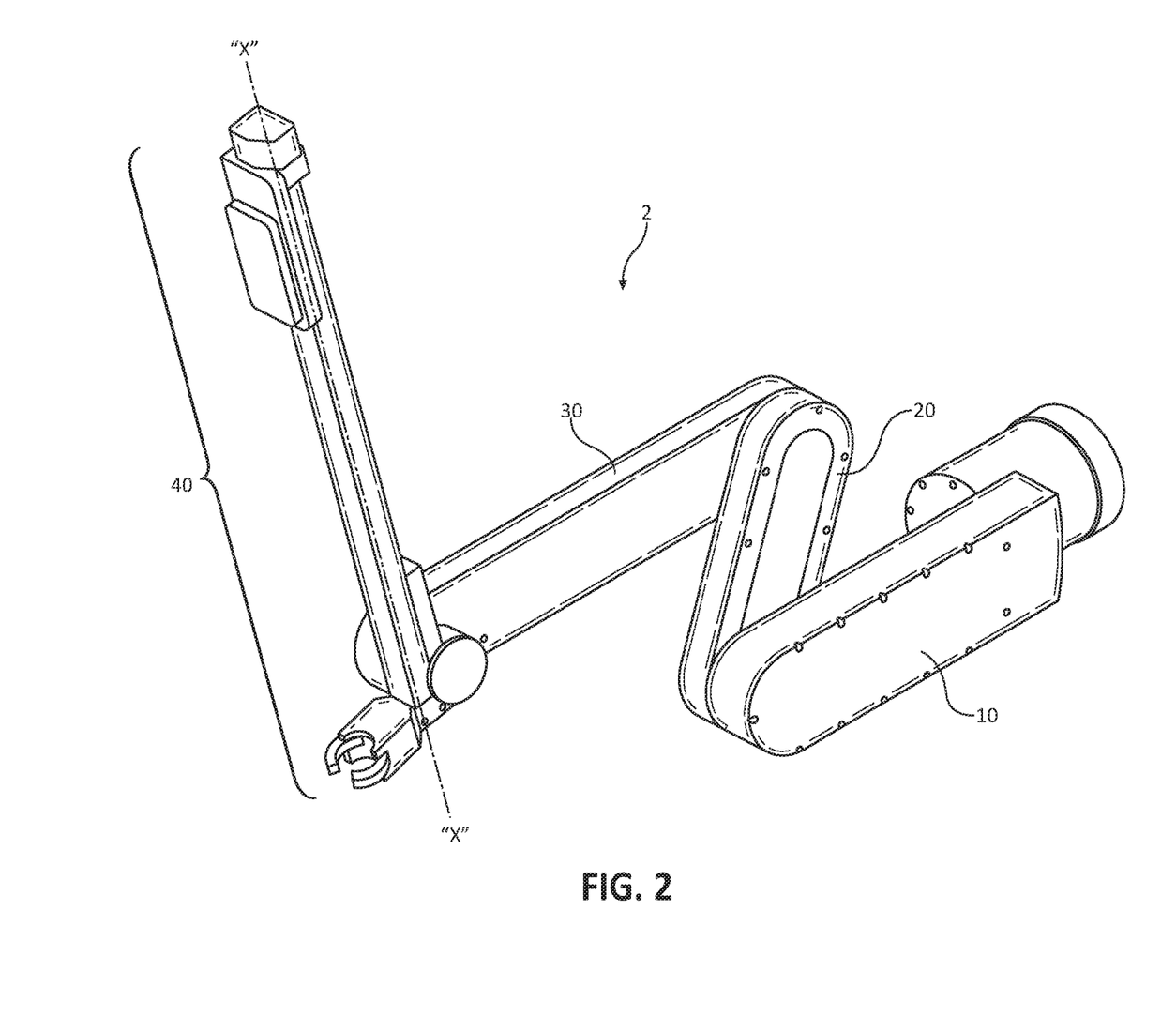
FIG. 2 is a perspective view of the robotic arm of FIG. 1.

Referring initially to FIGS. 1 and 2, a surgical system, such as, for example, a robotic surgical system 1, generally includes a plurality of surgical robotic arms 2, 3 and a surgical instrument 200 removably coupled to a slide rail 40 of surgical robotic arms 2, 3. Robotic surgical system 1 further includes a control device 4 and an operating console 5 coupled with control device 4. In some embodiments, surgical system 1 may include only one robotic arm (e.g., used for camera guidance).

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) may be set up to activate the drives, in particular by means of a computer program, in such a way that robotic arms 2, 3 and the attached surgical instrument 200 execute a desired movement according to a movement defined by means of manual input devices 7, 8. Control device 4 may also be set up in such a way that it regulates the movement of robotic arms 2, 3.

Robotic surgical system 1 is configured for use on a patient "P" lying on a surgical table "ST" to be treated in a minimally invasive manner by means of a surgical instrument, e.g., an electromechanical surgical instrument 200. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 200, may also be attached to the additional robotic arm.

Figure 3:
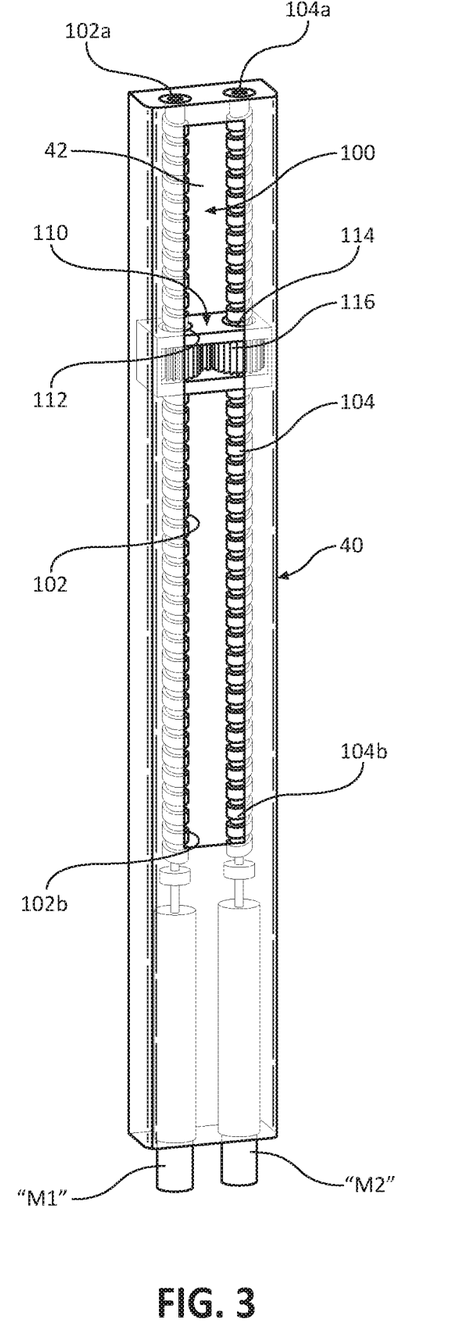
FIG. 3 is a perspective view of a multi-directional movement mechanism of the robotic arm of FIG. 2 configured to move a surgical instrument in a plurality of directions.

Control device 4 may control a plurality of motors, e.g., motors (Motor 1 . . . n), with each motor configured to drive movement of robotic arms 2, 3 in a plurality of directions. Further, control device 4 may control a motor assembly (not shown) of an instrument drive unit that drives various operations of surgical instrument 200. In addition, control device 4 may control the operation of first and second motors, such as, for example, canister motors "M1," "M2" (FIG. 3) of robotic arm 2, which are configured to drive a rotation and/or an axial movement of surgical instrument 200, as will be described in detail below.

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated by reference herein.

With reference to FIG. 2, the robotic arm 2 includes a plurality of elongate links or elongate members 10, 20, 30, 40 pivotably coupled to one another through joints. Elongate link or slide rail 40 is the terminal link of robotic arm 2 and is configured to be coupled to a surgical instrument 200 (FIGS. 1 and 6), which may be an electromechanical surgical instrument, an electrosurgical instrument, and/or an instrument drive unit. Elongate links 10, 20, 30, 40 together provide for multiple degrees of freedom of movement of surgical instrument 200 when surgical instrument 200 is coupled to elongate link or slide rail 40.

With reference to FIGS. 3-6, elongate link or slide rail 40 includes a multi-directional movement mechanism 100 configured to axially move surgical instrument 200 along a longitudinal axis "X" (FIG. 2) of elongate link or slide rail 40 and to rotate surgical instrument 200 about its longitudinal axis, as will be described in detail below. Multi-directional movement mechanism 100 of robotic arm 2 generally includes a left-handed lead screw 102, a right-handed lead screw 104, and a slider 110 axially movable along lead screws 102, 104, but prevented from rotating relative to lead screws 102, 104. Left-handed lead screw has a left-handed screw thread, and right-handed lead screw has a right-handed screw thread such that the screw threads for lead screws 102, 104 twist in opposite directions. Lead screws 102, 104 are disposed in parallel relation to one another within a cavity 42 defined in elongate link or slide rail 40. Lead screws 102, 104 are rotatable within elongate link or slide rail 40 while also being axially restrained within elongate link or slide rail 40.

Lead screws 102, 104 each include a respective first end 102a, 104a rotatably connected to a first end of elongate link or slide rail 40, and a respective second end 102b, 104b. Second ends 102b, 104b of lead screws 102, 104 have or are coupled to motors, for example, a first canister motor "M1," and a second canister motor "M2." In some embodiments, gears, universal shafts, flexible shafts, brakes, and/or encoders may be associated with motors "M1," "M2." Motors "M1," "M2" drive a rotation of lead screws 102, 104 and are electrically connected to control device 4 (FIG. 1), via cables or a wireless connection, which is configured to independently control the actuation of motors "M1," "M2."

Slider 110 of multi-directional movement mechanism 100 is slidably disposed within cavity 42 of elongate link or slide rail 40 and operably coupled to lead screws 102, 104. Slider 110 has a generally rectangular shape, but it is contemplated that slider 110 may assume any suitable shape. Slider 110 defines a first passageway 112 therethrough that has left-handed lead screw 102 extending therethrough, and a second passageway 114 therethrough that has right-handed lead screw 104 extending therethrough. Slider 110 further defines an opening 116 in a side thereof. Slider 110 is configured to be coupled to surgical instrument 200 such that axial movement of slider 110 relative to and along lead screws 102, 104 results in a corresponding axial movement of surgical instrument 200.

Figure 4:
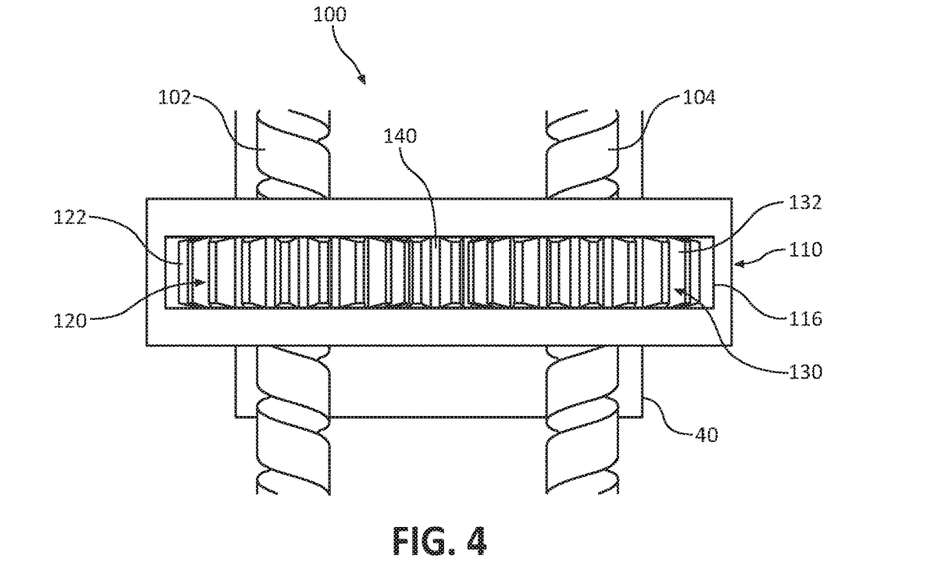
FIG. 4 is a front view of the multi-directional movement mechanism of the robotic arm of FIG. 3.
Figure 5:
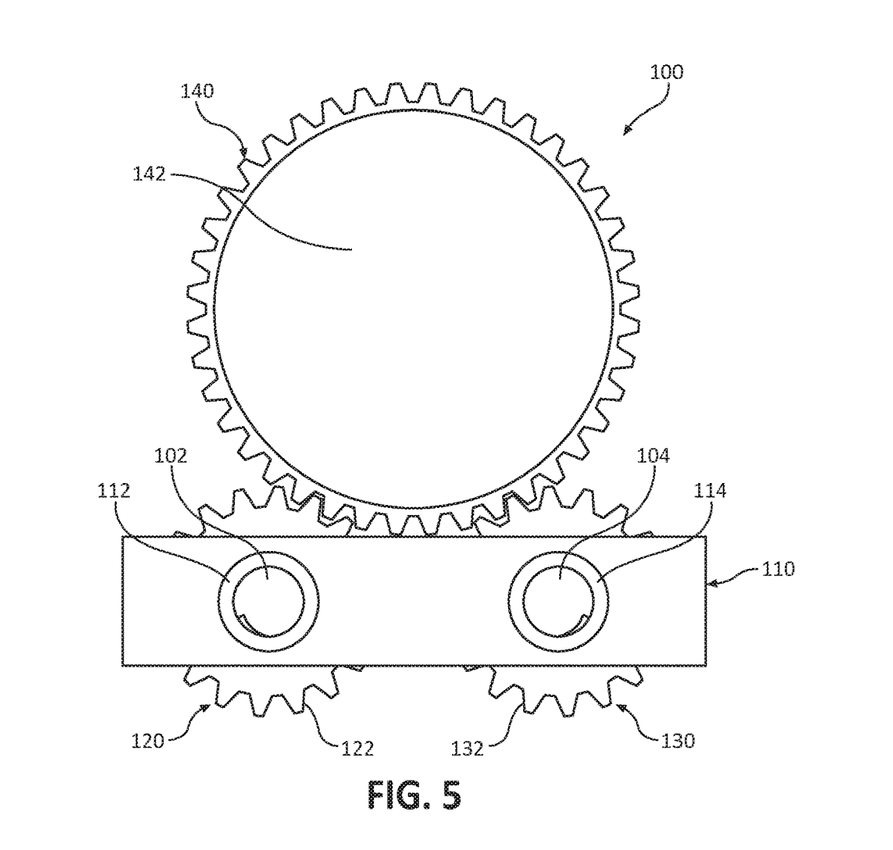
FIG. 5 is a top view of the multi-directional movement mechanism of FIG. 3.
Figure 6:
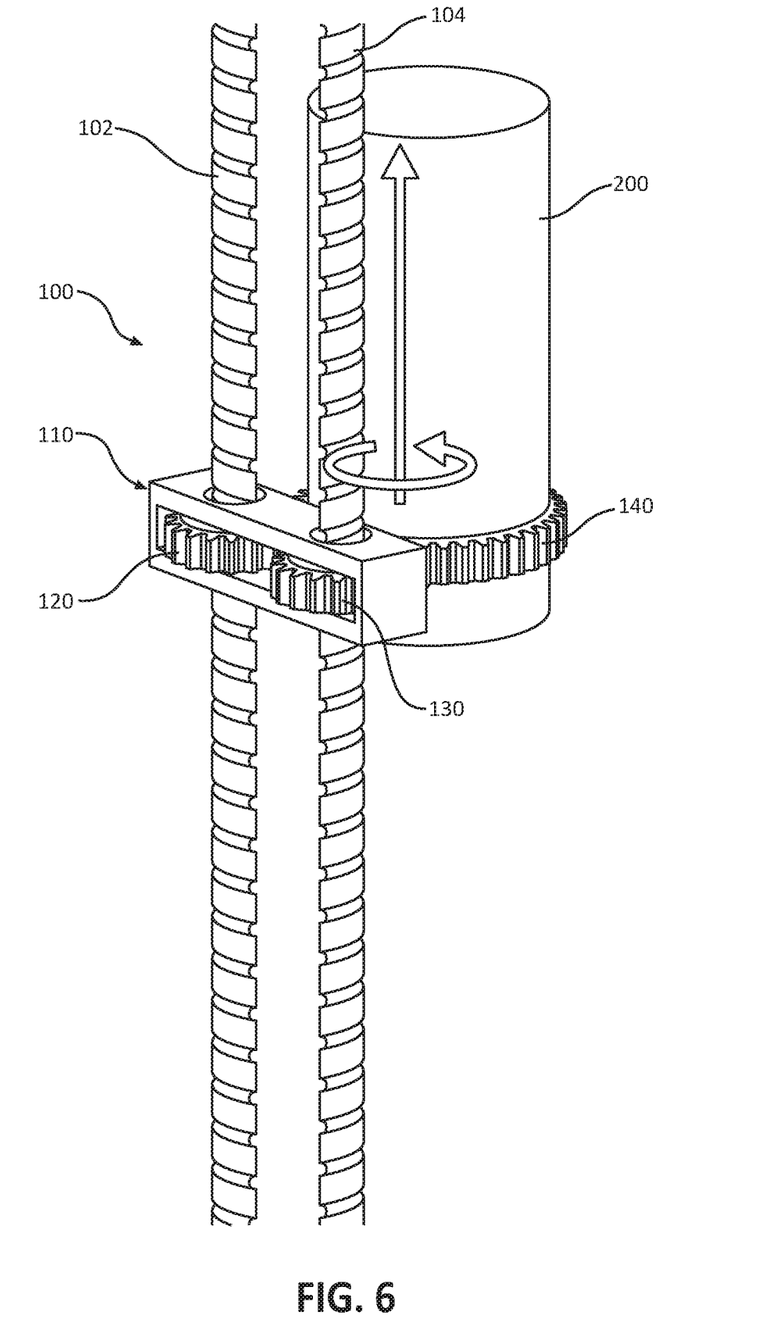
FIG. 6 is a perspective view of the multi-direction movement mechanism of FIG. 3 coupled to a surgical instrument.

With reference to FIGS. 4-6, multi-directional movement mechanism 100 includes a first shroud or nut 120 and a second shroud or nut 130, and a gear or cogwheel 140 operably coupled to the first and second nuts 120, 130. First and second nuts 120, 130 are each rotatably disposed within slider 110 and axially restrained therein. First and second nuts 120, 130 are coaxial with respective first and second passageways 112, 114 of slider 110 such that left-handed lead screw 102 extends through first nut 120, and right-handed lead screw 104 extends through second nut 130. First and second nuts 120, 130 have threaded inner surfaces (not explicitly shown) threadingly engaging the thread form of respective lead screws 102, 104.

First and second nuts 120, 130 each have a geared or toothed outer surface 122, 132 that projects outwardly from side opening 116 defined in slider 110. It is contemplated that toothed outer surfaces 122, 132 may be spur gears integrally formed with first and second nuts 120, 130.

Rotation of lead screws 102, 104 in the same direction as one another and relative to first and second nuts 120, 130 will result in a force being directed on first and second nuts 120, 130 that would tend to move nuts 120, 130 along lead screws 102, 104 in opposite longitudinal directions if nuts 120, 130 were not constrained within slider 110. However, since nuts 120, 130 are axially restrained within slider 110, nuts 120, 130 cannot move in opposite longitudinal directions along lead screws 102, 104. Nuts 120, 130 are driven to move in opposite longitudinal directions upon rotation of leads screws 102, 104 in the same direction due to lead screws 102, 104 having screw threads that run in opposite directions from each other.

Cogwheel 140 of multi-directional movement mechanism 100 is in operable engagement with geared outer surfaces 122, 132 of respective first and second nuts 120, 130. As such, a rotation of first and second nuts 120, 130 in the same direction (e.g., clockwise or counter-clockwise) will result in a rotation of cogwheel 140 in the opposite direction, whereas an attempt at rotating first and second nuts 120, 130 in opposite directions will result in no rotation of first and second nuts 120, 130 and no rotation of cogwheel 140.

Cogwheel 140 defines an opening 142 therethrough configured for receipt of surgical instrument 200. In some embodiments, opening 142 is configured to capture surgical instrument 200 therein such that rotation of cogwheel 140, as a result of rotation of first and second nuts 120, 130 in the same direction, will effect a rotation of surgical instrument 200. In some embodiments, multi-directional movement mechanism 100 may include an intermediary gear, for example, a rack (not explicitly shown) interposed between cogwheel 140 and first and second nuts 120, 130 to transfer movement from first and second nuts 120, 130 to cogwheel 140.

With continued reference to FIGS. 5 and 6, cogwheel 140 is coupled to slider 110 in such a way that cogwheel 140 is rotatable relative to slider 110 and axially movable along lead screws 102, 104 with slider 110. It is contemplated that cogwheel 140 may be coupled to slider 110 via any suitable fastening arrangement to prevent cogwheel 140 from sliding relative to slider 110 while also allowing cogwheel 140 to rotate relative to slider 110.

Figure 7:
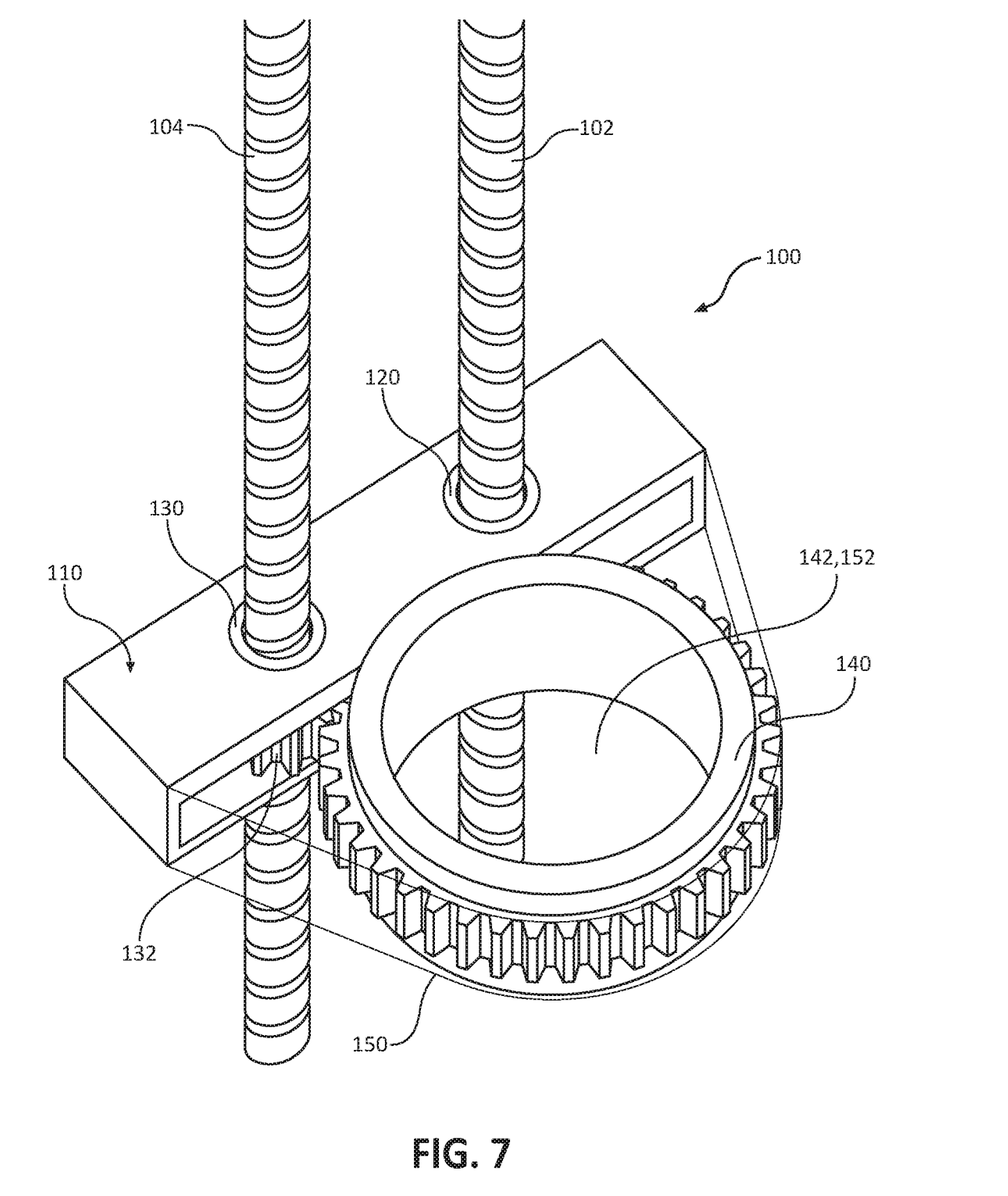
FIG. 7 is another embodiment of a multi-directional movement mechanism of the robotic arm of FIG. 3.

For example, with reference to FIG. 7, multi-directional movement mechanism 100 may further include a housing or interface 150 connected to slider 110. Housing 150 extends laterally from a side of slider 110. Housing 150 rotatably supports cogwheel 140 therein and prevents cogwheel 140 from moving axially relative thereto. As such, when slider 110 moves or slides along and relative to lead screws 102, 104, housing 150 with cogwheel 140 also moves or slides relative to lead screws 102, 104. Housing 150 defines a central passageway 152 therethrough configured for passage of surgical instrument 200. Central passageway 152 of housing 152 is coaxial with opening 142 defined in cogwheel 140.

With reference to FIGS. 8A-12B, an operation of multi-directional movement mechanism 100 will be described in detail. As will be appreciated, the axial movement of slider 110 and the rotation of cogwheel 140 depend on the direction of rotation of lead screws 102, 104. When lead screws 102, 104 are rotated in any direction, nuts 120, 130 always tend to both rotate and move up or down along respective lead screws 102, 104. The rotation of lead screws 102, 104 in opposite directions results in an axial movement of slider 110 and the attached surgical instrument 200, whereas the rotation of lead screws 102, 104 in the same direction results in a rotation of cogwheel 140 and the attached surgical instrument 200, and no axial movement of slider 110 and the attached surgical instrument 200.

Figure 8A:
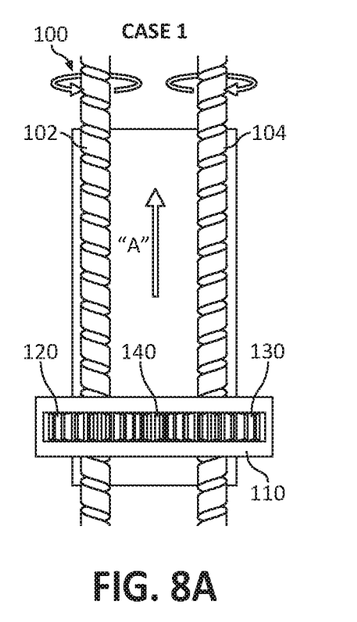
Figure 8B:
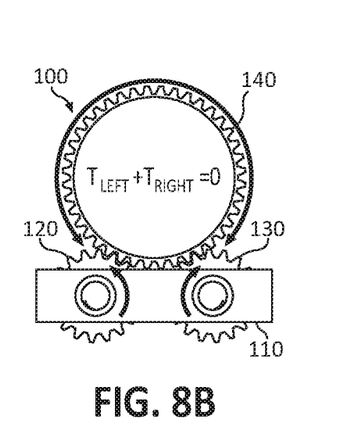

In particular, with reference to FIGS. 8A and 8B, to cause slider 110, and an attached surgical instrument 200 (FIG. 6), to move in an upward or proximal direction indicated by arrow "A" in FIG. 8A, first motor "M1" (FIG. 3) of multi-directional movement mechanism 100 is actuated to rotate left-handed lead screw 102 in a counter-clockwise direction while second motor "M2" of multi-directional movement mechanism 100 is actuated to rotate right-handed lead screw 104 in a clockwise direction. When left-handed lead screw 102 is rotated in the counter-clockwise direction, first nut 120 initially tends to rotate counter-clockwise integrally with left-handed lead screw 102, and when right-handed lead screw 104 is rotated in the clockwise direction, second nut 130 initially tends to rotate clockwise integrally with right-handed lead screw 104. However, since cogwheel 140 of multi-directional movement mechanism 100 is operably coupled to first and second nuts 120, 130, the rotation of first and second nuts 120, 130 in opposite directions is prevented, which results in lead screws 102, 104 rotating relative to first and second nuts 120, 130 rather than integrally therewith.

The rotation of left-handed lead screw 102 counter-clockwise relative to first nut 120 drives movement of first nut 120 in the upward or proximal direction, and rotation of right-handed lead screw 104 clockwise relative to second nut 130 also drives movement of second nut 130 in the upward or proximal direction. When first and second nuts 120, 130 are moved upwardly or proximally along lead screws 102, 104, slider 110 also moves upwardly or proximally relative to lead screws 102, 104 due to first and second nuts 130, 140 being axially restrained within slider 110. Since slider 110 is coupled to cogwheel 140, and cogwheel 140 is coupled to surgical instrument 200, upward or proximal movement of slider 110 results in an upward or proximal movement of surgical instrument 200.

Figure 9A:
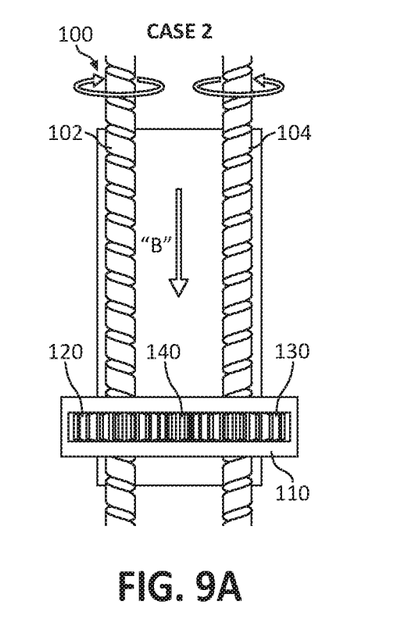
Figure 9B:
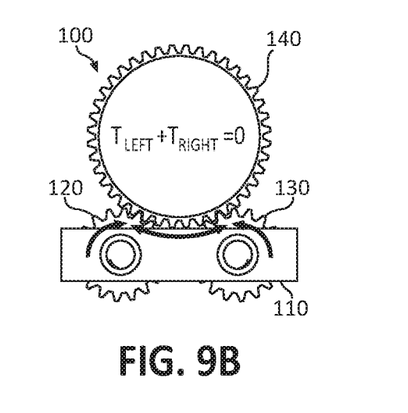

With reference to FIGS. 9A and 9B, to cause slider 110, and in turn surgical instrument 200 (FIG. 6), to move in a downward or distal or distal direction indicated by arrow "B" in FIG. 9A, first motor "M1" of multi-directional movement mechanism 100 is actuated to rotate left-handed lead screw 102 in a clockwise direction while second motor "M2" of multi-directional movement mechanism 100 is actuated to rotate right-handed lead screw 104 in a counter-clockwise direction. When left-handed lead screw 102 is rotated in the clockwise direction, first nut 120 initially tends to rotate clockwise integrally with left-handed lead screw 102, and when right-handed lead screw 104 is rotated in the counter-clockwise direction, second nut 130 initially tends to rotate counter-clockwise integrally with right-handed lead screw 104. However, since cogwheel 140 is operably coupled to first and second nuts 120, 130, the rotation of first and second nuts 120, 130 in opposite directions is prevented, which results in lead screws 102, 104 rotating relative to first and second nuts 120, 130 rather than integrally therewith.

The rotation of left-handed lead screw 102 clockwise relative to first nut 120 drives movement of first nut 120 in the downward or distal direction, and rotation of right-handed lead screw 104 counter-clockwise relative to second nut 130 also drives movement of second nut 130 in the downward or distal direction. When first and second nuts 120, 130 are moved downwardly or distally along lead screws 102, 104, slider 110 also moves downwardly or distally relative to lead screws 102, 104 due to nuts 120, 130 being axially restrained within slider 110. Since slider 110 is coupled to cogwheel 140, and cogwheel 140 is coupled to surgical instrument 200, downward or distal movement of slider 110 results in a downward or distal movement of surgical instrument 200.

Figure 10A:
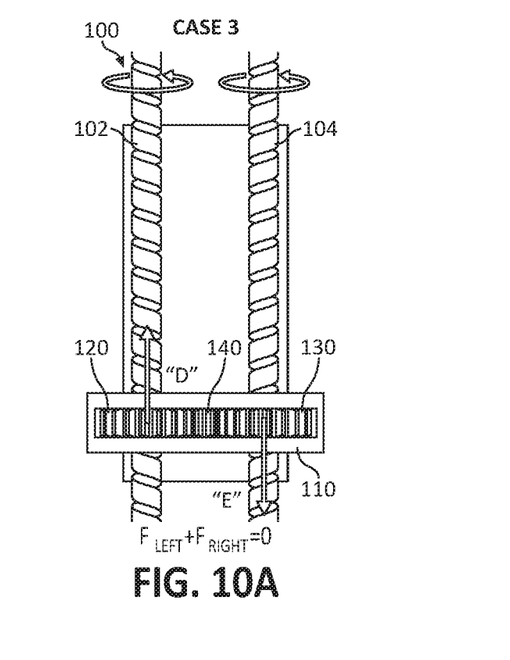
Figure 10B:
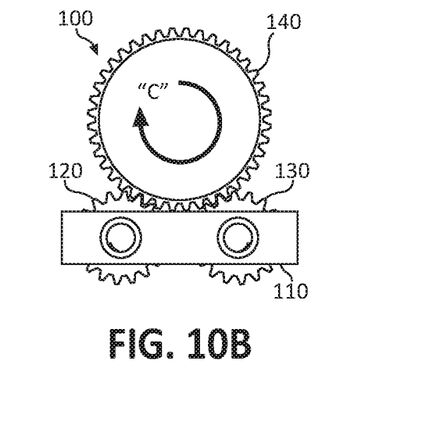

With reference to FIGS. 10A and 10B, to cause cogwheel 140, and the attached surgical instrument 200 (FIG. 6), to rotate in a clockwise direction as indicated by arrow "C" in FIG. 10B, first and second motors "M1," "M2" of multi-directional movement mechanism 100 are actuated to rotate both left-handed lead screw 102 and right-handed lead screw 104 in a counter-clockwise direction. When left-handed lead screw 102 is rotated in the counter-clockwise direction, first nut 120 tends to move in the upward or proximal direction indicated by arrow "D" in FIG. 10A, while when right-handed lead screw 104 is rotated in the counter-clockwise direction, second nut 130 tends to move in the downward or distal direction indicated by arrow "E" in FIG. 10A. Since first and second nuts 120, 130 are being driven in opposite longitudinal directions, no movement of slider 110 results, and first and second nuts 120, 130 begin to rotate counter-clockwise integrally with lead screws 102, 104 rather than relative to lead screws 102, 104. The rotation of first and second nuts 120, 130 in the counter-clockwise direction drives a rotation of cogwheel 140 in the clockwise direction. When surgical instrument 200 (FIG. 6) is non-rotatably received within cogwheel 140, the clockwise rotation of cogwheel 140 causes surgical instrument 200 to rotate therewith.

Figure 11A:
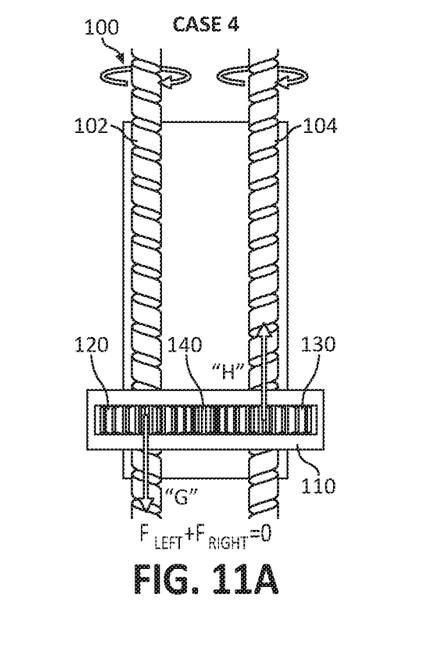
Figure 11B:
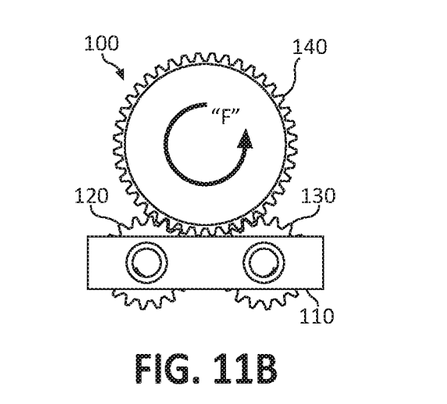

With reference to FIGS. 11A and 11B, to cause cogwheel 140, and in turn surgical instrument 200 (FIG. 6), to rotate in a counter-clockwise direction as indicated by arrow "F," motors "M1," "M2" of multi-directional movement mechanism 100 are actuated to rotate both left-handed lead screw 102 and right-handed lead screw 104 in a clockwise direction. When left-handed lead screw 102 is rotated in the clockwise direction, first nut 120 tends to move in the downward or distal direction indicated by arrow "G" in FIG. 11A, while when right-handed lead screw 104 is rotated in the clockwise direction, second nut 130 tends to move in the upward or proximal direction as indicated by arrow "H" in FIG. 11A. Since first and second nuts 120, 130 are being driven in opposite longitudinal directions, no movement of slider 110 results, and first and second nuts 120, 130 begin to rotate clockwise integrally with lead screws 102, 104 rather than relative to lead screws 102, 104. The rotation of first and second nuts 102, 104 in the clockwise direction drives a rotation of cogwheel 140 in the counter-clockwise direction. When surgical instrument 200 (FIG. 6) is non-rotatably received within cogwheel 140, the counter-clockwise rotation of cogwheel 140 causes surgical instrument 200 to rotate therewith.

Figure 12A:
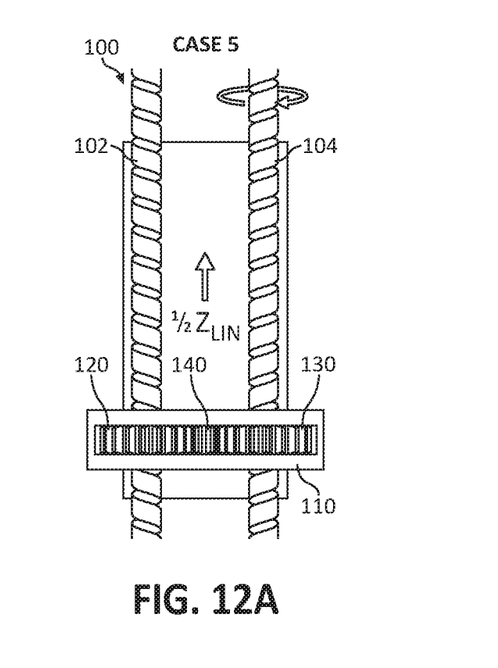
Figure 12B:
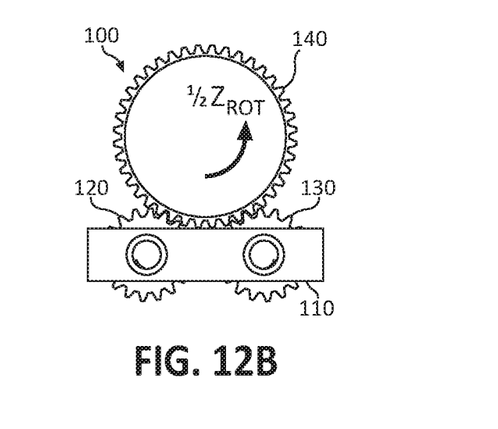

With reference to FIGS. 12A and 12B, to simultaneously drive a rotation of cogwheel 140 and an axial movement of slider 110, only one of first and second motors "M1," "M2" of multi-directional movement mechanism 100 is actuated. For example, to simultaneously move cogwheel 140 in an upward or proximal direction and rotate cogwheel 140 in a counter-clockwise direction, second motor "M2" is actuated to rotate right-handed lead screw 104 in a clockwise direction. When right-handed lead screw 104 is rotated in the clockwise direction, second nut 130 tends to rotate clockwise integrally therewith. Rotation of second nut 130 in the clockwise direction causes cogwheel 140 to rotate in the counter-clockwise direction due to cogwheel 140 being operably engaged to second nut 130. Rotation of cogwheel 140 in the counter-clockwise direction will result in a corresponding rotation of surgical instrument 200 (FIG. 6) when surgical instrument 200 is non-rotatably received therein.

Rotation of cogwheel 140 in the counter-clockwise direction will also result in a clockwise rotation of first nut 120 due to cogwheel 140 being operably engaged to first nut 120. The rotation of first nut 120 in a clockwise direction will not result in a corresponding rotation of left-handed lead screw 102 because left-handed lead screw 102 is prevented from being rotated by anything other than an actuation of first motor "M1." Thus, first nut 120 will rotate relative to left-handed lead screw 102 resulting in movement of first nut 120, and slider 110, in the upward or proximal direction along lead screws 102, 104. As such, if surgical instrument 200 is non-rotatably disposed within cogwheel 140, surgical instrument 200 will be simultaneously moved upwardly or proximally and rotated in a counter-clockwise direction.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A robotic arm configured to support and operate a surgical instrument, comprising:
    a slider;
    first and second nuts rotatably disposed within the slider and each having a geared outer surface;
    a gear operably coupled to the geared outer surface of each of the first and second nuts;
    a left-handed lead screw extending through the slider and threadingly engages the first nut; and
    a right-handed lead screw disposed in parallel relation with the left-handed lead screw and extending through the slider and threadingly engages the second nut, wherein a rotation of at least one of the left-handed lead screw or the right-handed lead screw effects a rotation of the gear relative to the slider or an axial movement of the slider and the gear along the lead screws, wherein the gear is configured for non-rotatable receipt of a surgical instrument such that rotation of the gear effects rotation of a surgical instrument when a surgical instrument is disposed therein.

2. The robotic arm according to claim 1, wherein rotation of the lead screws in opposite directions relative to one another causes the lead screws to rotate relative to the first and second nuts to drive an axial movement of the first and second nuts and the slider along the lead screws.

3. The robotic arm according to claim 1, wherein rotation of the lead screws in the same direction relative to one another rotates the first and second nuts to drive a rotation of the gear relative to the slider.

4. The robotic arm according to claim 3, wherein no axial movement of the slider and the gear along the lead screws results in response to the lead screws being rotated in the same direction.

5. The robotic arm according to claim 1, further comprising a housing connected to the slider, the gear rotatably disposed within the housing and axially constrained within the housing, wherien the housing and the slider are configured to move axially together along the lead screws.

6. The robotic arm according to claim 5, wherein the housing defines a passageway therethrough configured for passage of a surgical instrument.

7. The robotic arm according to claim 1, further comprising:
a first motor operably coupled to the left-handed lead screw; and
a second motor operably coupled to the right-handed lead screw such that the lead screws are independently rotatable relative to one another.

8. The robotic arm according to claim 1, further comprising an elongate link having the slider slidably disposed therein and the lead screws rotatably disposed therein, the lead screws axially fixed within the elongate link.

9. The robotic arm according to claim 1, wherein the slider defines a first passageway therethrough and a second passageway therethrough, the first nut disposed coaxially with the first passageway and the second nut disposed coaxially with the second passageway.

10. The robotic arm according to claim 9, wherein the slider defines a side opening therein, the geared outer surface of each of the first and second nuts projecting outwardly through the side opening.

11. A robotic surgical system, comprising:
a surgical instrument; and
a robotic arm including:
a first elongate link;
a second elongate link pivotably coupled to the first elongate link;
a slider slidably disposed within the second elongate link;
first and second nuts rotatably disposed within the slider and each having a geared outer surface;
a gear operably coupled to the geared outer surface of each of the first and second nuts, the gear configured to non-rotatably receive the surgical instrument;
a left-handed lead screw extending through the slider and threadingly engages the first nut; and
a right-handed lead screw disposed in parallel relation with the left-handed lead screw and extending through the slider and threadingly engages the second nut, wherein a rotation of at least one of the left-handed lead screw or the right-handed lead screw effects a rotation of the gear relative to the slider or an axial movement of the slider and the gear along the lead screws, wherein rotation of the gear effects rotation of the surgical instrument when the surgical instrument is disposed in the gear.

12. The robotic surgical system according to claim 11, wherein rotation of the lead screws in opposite directions relative to one another causes the lead screws to rotate relative to the first and second nuts to drive an axial movement of the first and second nuts and the slider along the lead screws.

13. The robotic surgical system according to claim 11, wherein rotation of the lead screws in the same direction relative to one another rotates the first and second nuts to drive a rotation of the gear relative to the slider.

14. The robotic surgical system according to claim 13, wherein no axial movement of the slider and the gear along the lead screws results in response to the lead screws being rotated in the same direction.

15. The robotic surgical system according to claim 11, wherein the robotic arm further includes a housing connected to the slider, the gear rotatably disposed within the housing and axially constrained within the housing, wherein the housing and the slider are configured to move axially together along the lead screws.

16. The robotic surgical system according to claim 15, wherein the housing defines a passageway therethrough configured for passage of the surgical instrument.

17. The robotic surgical system according to claim 11, wherein the robotic arm further includes:
a first motor operably coupled to the left-handed lead screw; and
a second motor operably coupled to the right-handed lead screw such that the lead screws are independently rotatable.

18. The robotic surgical system according to claim 11, wherein the lead screws are axially fixed within the second elongate link and the slider is axially movable within the second elongate link.

19. The robotic surgical system according to claim 11, wherein the slider defines a first passageway therethrough and a second passageway therethrough, the first nut disposed coaxially with the first passageway and the second nut disposed coaxially with the second passageway.

20. The robotic surgical system according to claim 19, wherein the slider defines a side opening therein, the geared outer surface of each of the first and second nuts projecting outwardly through the side opening.

* * * * *